US00PP23034P2

(12) United States Plant Patent
Shimmen

(10) Patent No.: US PP23,034 P2
(45) Date of Patent: Sep. 11, 2012

(54) ***LOMANDRA* PLANT NAMED 'LOMLON'**

(50) Latin Name: *Lomandra hybrida*
Varietal Denomination: Lomlon

(75) Inventor: Ian Shimmen, Mt. Evelyn (AU)

(73) Assignee: Bushland Flora, Mt. Evelyn (AU)

( * ) Notice: Subject to any disclaimer, the term of this patent is extended or adjusted under 35 U.S.C. 154(b) by 0 days.

(21) Appl. No.: 13/068,593

(22) Filed: May 16, 2011

(51) Int. Cl.
*A01H 5/00* (2006.01)

(52) U.S. Cl. ..... Plt./373; Plt./263.1; Plt./384

(58) Field of Classification Search ..... Plt./373, Plt./263.1, 384
See application file for complete search history.

*Primary Examiner* — June Hwu
*Assistant Examiner* — Louanne Krawczewicz Myers
(74) *Attorney, Agent, or Firm* — Mark P. Bourgeois

(57) ABSTRACT

A new cultivar of *Lomandra* plant named 'Lomlon' that is characterized by narrow flat green leaves, the absence of dead or brown leaves and vigorous growth in a variety of soil types.

1 Drawing Sheet

Botanical classification: *Lomandra hybrida.*
Variety denomination: 'Lomlon'.

BACKGROUND OF THE INVENTION

The present invention relates to a new and distinct cultivar of *Lomandra* plant botanically known as *Lomandra hybrida* and hereinafter referred to by the cultivar name 'Lomlon'.

The new *Lomandra* is the product of a breeding program conducted by the inventor in Mount Evelyn, Victoria, Australia. The objective of the breeding program is to create new *Lomandra* cultivars with narrow leaves.

'Lomlon' originated from the crossing in 2004 of the female or seed parent an unnamed *Lomandra longifolia* cultivar and the male or pollen parent an unnamed *Lomandra confertifolia* cultivar. The resulting seeds were subsequently planted and grown. The cultivar 'Lomlon' was selected by the inventor in 2005 as a single plant within the progeny of the stated cross in Mount Evelyn, Victoria, Australia.

Asexual reproduction of the new cultivar 'Lomlon' first occurred by tissue culture in 2005 in Mount Evelyn, Victoria, Australia. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Lomandra* cultivar 'Lomlon'. These traits in combination distinguish 'Lomlon' as a new and distinct cultivar apart from other existing known varieties of *Lomandra.*

1. *Lomandra* 'Lomlon' exhibits narrow flat green leaves.
2. *Lomandra* 'Lomlon' does not exhibit dead or brown leaves.
3. *Lomandra* 'Lomlon' exhibits vigorous growth in a variety of soil types.

The closest comparison cultivars are *Lomandra* 'Little Pal' (not patented) and *Lomandra* 'LM300' (U.S. Plant Pat. No. 15,420).

'Lomlon' is distinguishable from 'Little Pal' by the following characteristics:

1. 'Lomlon' has stronger and narrower leaves.
2. 'Lomlon' has a taller overall height.
3. 'Lomlon' has flowers held on longer peduncles than 'Little Pal'.

'Lomlon' is distinguishable from 'LM300' by the following characteristics:

1. 'Lomlon' has shorter and wider leaves.
2. 'Lomlon' has stronger leaves.
3. 'Lomlon' has flowers held on longer peduncles than 'LM300'.

'Lomlon' is distinguishable from the female or seed parent unnamed *Lomandra longifolia* cultivar by the following characteristics:

1. 'Lomlon' has narrower leaves.

'Lomlon' is distinguishable from the male or pollen parent unnamed *Lomandra confertifolia* cultivar by the following characteristics:

1. 'Lomlon' has wider leaves.

BRIEF DESCRIPTION OF THE DRAWING

The accompanying photograph illustrates the distinguishing traits of *Lomandra* 'Lomlon'. The plant in the photograph shows an overall view of a 1 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Lomandra* cultivar named 'Lomlon'. Data was collected in Mount Evelyn, Victoria, Australia from 18 month old outdoor grown plants in 20 cm. diameter containers. The time of year was Fall in the Southern Hemisphere and the average temperature was 26 degrees Centigrade during the day and 10 degrees Centigrade at night. Color determinations are in accordance with The Royal Horticultural Society Colour Chart 2007 edition, except where general color terms of ordinary dictionary significance are used. The growing requirements are similar to the species. 'Lomlon' has not been tested under all possible conditions and phenotypic differences may be observed with variations in environmental, climatic, and cultural conditions, however, without any variance in genotype.

Botanical classification: *Lomandra* 'Lomlon'.

Annual or perennial: Perennial.

Parentage: 'Lomlon' is the product of the female or seed parent an unnamed *Lomandra longifolia* cultivar and the male or pollen parent an unnamed *Lomandra confertifolia* cultivar.

Vigor: Strong.

Growth habit: Upright.

Plant shape: Tufting grass.

Suitable container size: 14 cm. and larger pots.

Height: 90 cm. in height.

Width: 90 to 120 cm. in width.

Low temperature tolerance: −8° Centigrade.

High temperature tolerance: 45° Centigrade.

Propagation: Tissue culture.

Time to initiate roots in summer: 15 days to initiate roots at 21° Centigrade.

Time to initiate roots in winter: 25 days to initiate roots at 15° Centigrade.

Time to produce a rooted cutting or liner in summer: 84 days at 21° Centigrade.

Time to produce a rooted cutting or liner in winter: 140 days at 15° Centigrade.

Crop time: 6 to 12 months.

Root system: Fine and fibrous.

Rhizomes:

*Rhizome dimensions.*—4 cm. in length and 0.5 cm. in diameter.

*Rhizome texture.*—Smooth.

*Rhizome color.*—155C.

Foliage:

*Leaf arrangement.*—Tussock.

*Compound or single.*—Single.

*Leaf shape.*—Linear.

*Leaf apex.*—Praemorse.

*Leaf base.*—Sheathed.

*Leaf length.*—59.5 cm. in length.

*Leaf width.*—4 cm. in width.

*Texture.*—Glabrous both sides.

*Pubescence.*—Absent.

*Leaf margin.*—Entire.

*Venation pattern.*—Linear.

*Young leaf color (upper surface).*—141B.

*Young leaf color (lower surface).*—141B.

*Mature leaf color (upper surface).*—141B.

*Mature leaf color (lower surface).*—141B.

*Vein color (upper surface).*—141B.

*Vein color (under surface).*—141B.

*Basal sheath color.*—158A.

*Basal leaf margin color.*—134A.

Flower:

*Inflorescence arrangement.*—Flowers arranged in panicles, male flowers only.

*Inflorescence dimensions.*—Average 30 mm. in height and 30 mm. in width.

*Quantity of flowers per inflorescence.*—Approximately 200.

*Quantity of flowers and buds per plant.*—Approximately 1000.

*Natural flowering season.*—Spring and summer.

*Rate of flower opening.*—1 week.

*Fragrance.*—Slight.

*Flower bud length.*—2.5 mm.

*Flower bud diameter.*—1.5 mm.

*Flower bud shape.*—Ovate.

*Bud color.*—166A.

*Rate of bud opening.*—3 to 4 days.

*Bract number.*—4 to 5.

*Bract shape.*—Elliptical.

*Bract dimensions.*—3 mm. in length and 1.5 mm. in width.

*Bract tip.*—Acute.

*Bract base.*—Fused.

*Bract margin.*—Entire.

*Bract color.*—200B (upper and lower surfaces).

*Flower aspect.*—Outward.

*Flower shape.*—Ovate.

*Flower dimensions.*—1.5 mm. in diameter and 2.5 mm. in height.

*Flower longevity.*—3 to 6 weeks.

*Number of petals.*—3.

*Fused or unfused.*—Fused.

*Petal shape.*—Ovate.

*Petal texture.*—Smooth both sides.

*Petal margin.*—Entire.

*Petal apex.*—Acute.

*Petal base.*—Fused.

*Petal length.*—2.5 mm.

*Petal width.*—1.5 mm.

*Petal color when opening (upper side).*—5A.

*Petal color when opening (under side).*—5A.

*Petal color fully opened (upper side).*—5A.

*Petal color fully opened (under side).*—5A.

*Petal color fading to.*—5A.

*Self-cleaning or persistent.*—Self-cleaning.

Calyx:

*Number.*—3.

*Calyx shape.*—Ovate.

*Calyx dimensions.*—1.5 mm. in length and 1 mm. in diameter.

*Calyx color.*—177B (upper and lower surfaces).

Peduncle:

*Peduncle dimensions.*—40 to 50 cm. in length with rectangular cross section 4 mm. by 1 mm.

*Peduncle angle.*—0 degrees from vertical.

*Peduncle strength.*—Medium.

*Peduncle color.*—143B.

Reproduction organs:

*Stamen number.*—6.

*Anther dimensions.*—0.5 mm in length and 0.5 mm. in diameter.

*Anther color.*—5A.

*Pollen.*—Absent.

Fruit and seed production: Fruit and seed production has not been observed.

Disease and pest resistance: Disease and pest resistance has not been observed.

The invention claimed is:

1. A new and distinct variety of *Lomandra* plant named 'Lomlon' as described and illustrated.

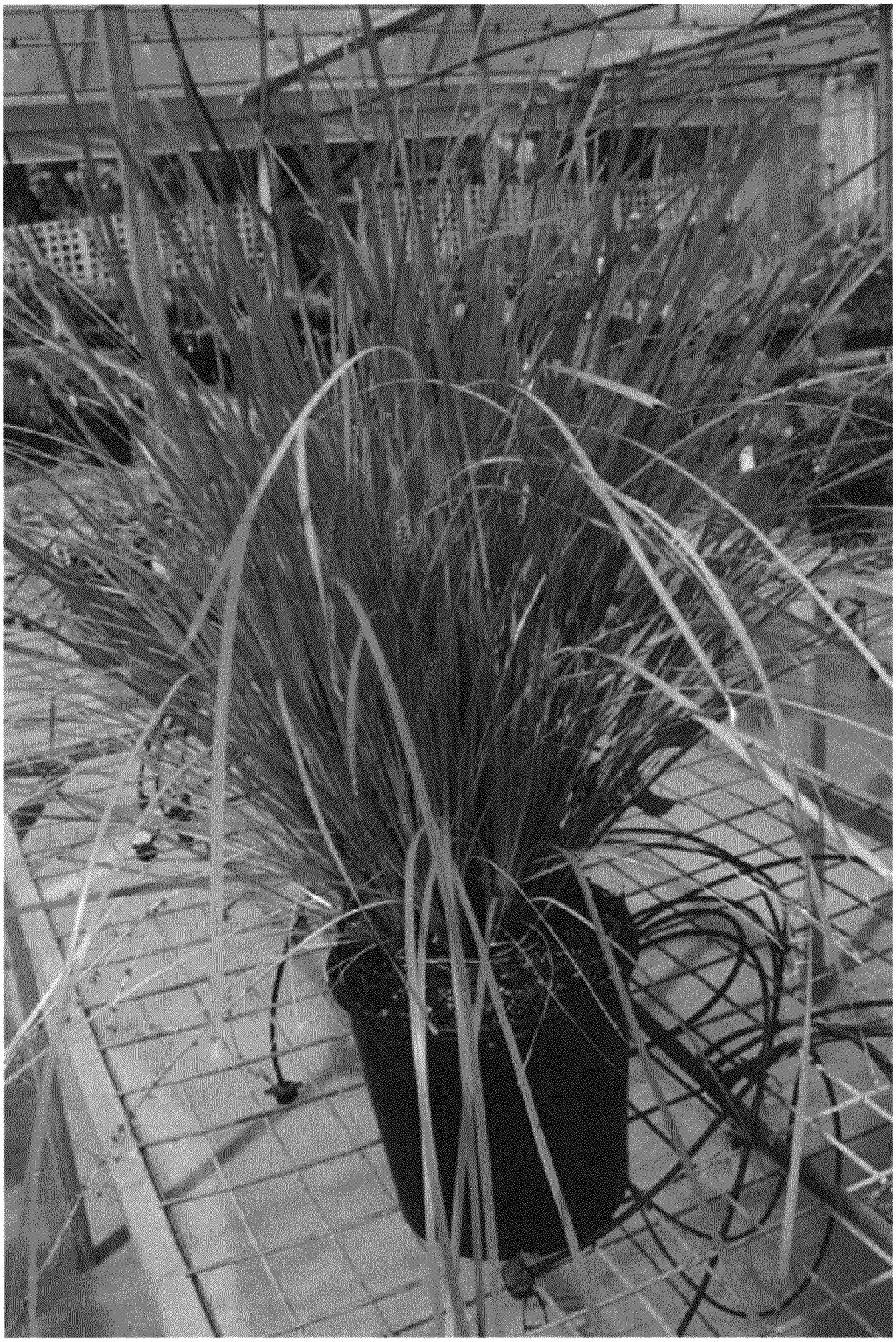

* * * * *